United States Patent [19]

Becker et al.

[11] Patent Number: 5,294,416
[45] Date of Patent: Mar. 15, 1994

[54] PROCESS FOR THE PREPARATION OF HBN

[75] Inventors: Abram Becker, Paris, France; Hyman Stollar, Beer Sheva, Israel

[73] Assignee: Bromine Compounds Limited, Israel

[21] Appl. No.: 943,768

[22] Filed: Sep. 11, 1992

Related U.S. Application Data

[62] Division of Ser. No. 621,350, Dec. 3, 1990, Pat. No. 5,169,972.

[30] Foreign Application Priority Data

Dec. 14, 1989 [IL] Israel .......................... 92705

[51] Int. Cl.$^5$ ................................. C01G 3/00
[52] U.S. Cl. .......................... 423/24; 423/23; 423/29
[58] Field of Search ............ 423/42, 364, 371.29, 423/34, 23, 24; 558/343

[56] References Cited

U.S. PATENT DOCUMENTS 4,925,642  5/1990  Stollar et al. .................. 558/343

OTHER PUBLICATIONS

*Ullmann's Encyclopedia of Industrial Chemistry*, vol. B3, (Fifth Edition, Gerhartz, Editor, VCH), pp. 6-16, 6-17 and 6-59.

Chemical Abstracts, vol. 112, No. 22, May 1988, p. 107.

*Primary Examiner*—David Brunsman
*Attorney, Agent, or Firm*—Lerner, David, Littenberg, Krumholz & Mentlik

[57] ABSTRACT

In a process for the preparation and the isolation of p-hydroxybenzonitrile (HBN), in which a p-halogenated phenol is reacted with cuprous cyanide in a suitable solvent, the reaction mixture obtained after the reaction of the p-halogenated phenol with cuprous cyanide has been substantially completed is contacted with an aqueous solution of a bromide salt and, optionally, an organic diluent, the aqueous and organic phases are separated, HBN is distilled out from the organic phase, an alkali metal cyanide is added to the aqueous phase and CuCN is filtered off from the resulting aqueous phase.

14 Claims, No Drawings

PROCESS FOR THE PREPARATION OF HBN

This is a division of application Ser. No. 07/621,350 filed Dec. 3, 1990, now U.S. Pat. No. 5,169,972.

THE FIELD OF THE INVENTION

The present invention relates to a process for the preparation and the isolation of p-hydroxybenzonitrile (HBN) from p-halogenated phenol, by reacting the p-halogenated phenol with cuprous cyanide (CuCN). More particularly the invention relates to processes by means of which HBN can be isolated and, at the same time, the reagent CuCN can be recovered from the reaction mixture.

BACKGROUND OF THE INVENTION

The reaction employing CuCN is well known in the art and is sometimes called the Rosenmund-von Braun Reaction. The reaction can schematically be represented by:

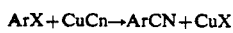

wherein X represents a halogen atom and the reaction is carried out at a temperature of about 150°–250° C. The reaction is carried out in a variety of solvents, the most commonly employed solvents being polar aprotic solvents such as dimethylformamide, dimethylacetamide and N-methyl-pyrrolidone. Commonly, an excess of CuCN is employed.

An example of such a process is the preparation of p-hydroxybenzonitrile (HBN) from p-halogenated phenol, which can conveniently be carried out in dimethylacetamide (DMA) as the solvent.

When the reaction is complete the solvent is normally distilled off and the nitrile product is obtained as a complex bound to the cuprous halide which is formed in the reaction. In order to isolate the nitrile product, the complex must be decomposed. Several methods are known in the art to effect this decomposition. In one such method (U.S. Pat. No. 3,259,646) concentrated hydrochloric acid and ferric chloride are added and the product is isolated by extraction into an organic solvent. According to another method [L. Freidman and H. Shechter, J.A.C.S., Vol. 26, pp. 2522-24 (1961)], ethylene diamine is added and the product is again isolated by solvent extraction. According to a further known method, the cuprous halide is dissolved in a aqueous solution containing 4 molar equivalents of NaCN and the product is extracted with an organic solvent.

The aforementioned and other known isolation methods present several serious drawbacks. The copper halide formed in the reaction is transformed into difficultly recoverable forms, which cannot be recycled as such. Furthermore, in the first mentioned method the formation of highly toxic hydrogen cyanide and cyanogen takes place. In the last two methods a considerable drawback is the alkaline nature of the solutions obtained, which prevents extraction of acidic nitriles into organic solvents.

In copending Israeli Patent Application No. 82694 of the same applicant, there is described a process for the preparation and the isolation of aromatic nitriles in which an aromatic halogenated compound is reacted with cuprous cyanide in a suitable solvent, comprising the steps of:

a) adding water to the reaction mixture obtained after the reaction of the aromatic halogenated compound with cuprous cyanide has been substantially completed;

b) adding an alkali metal cyanide to the resulting mixture;

c) separating the resulting CuCN suspension; and d) separating the organic phase to recover the aromatic nitrile; the amount of alkali metal cyanide added being substantially stoichiometric with the aromatic reagent employed in the reaction.

The above-described process, while representing a considerable improvement over processes known in the art before, still suffers from the drawback that the recovery of the aromatic nitrile requires difficult filtration operations. Such filtration operations are both cumbersome, time-consuming and expensive.

Another drawback of the process of IL 82694 is that the recovered CuCN is contaminated with organic materials, and is therefore obtained with relatively low purity.

SUMMARY OF THE INVENTION

It has now been found, and this is an object of the invention, that it is possible to provide a process which, while possessing all the advantages of the process of IL 82694, also provides the important advantage of requiring filtration from an aqueous mixture, rather than from an organic mixture, as in IL 82694, which results in a much easier and more efficient filtration.

It is another object of the invention to provide a process which is simple and easy to carry out, and which permits to obtain HBN of good purity and in high yield.

It is still another object of the invention to provide a process by which the reagent CuCN can be recovered in good yield and with high purity.

DETAILED DESCRIPTION OF THE INVENTION

The process according to the invention comprises:

a) contacting the reaction mixture obtained after the reaction of a p-halogenated phenol with cuprous cyanide in a suitable solvent has been substantially completed, with a mixture of an aqueous solution of a bromide salt and, optionally, with an organic diluent;

b) separating the aqueous and organic phases;

c) distilling HBN out from the organic phase;

d) adding an alkali metal cyanide to the aqueous phase; and e) filtering CuCN off from the resulting aqueous phase;

the amount of alkali metal cyanide added being substantially stoichiometric with the aromatic reagent employed in the reaction.

Thus, the CuCN recovery process can be suitably employed in any case in which CuX remains in the aqueous phase of the reaction mixture, after HBN has been removed.

Preferred p-halogenated phenols are those which are brominated or chlorinated.

According to a preferred embodiment of the invention, the alkali metal is sodium or potassium. Preferably, the bromide salt is selected from among sodium, potassium, calcium and ammonium bromide. Sodium bromide is the most preferred salt, for availability and cost reasons. Ammonium bromide is very convenient, because extraction therewith is both easy and quick. However, work-up with ammonium bromide requires additional separation treatments which are inconvenient.

The total quantity of bromide salt in the contact step ranges from 4.5 to 9 moles per mole of CuCN taken for reaction and preferably in the range 5 to 7.5 moles of bromide salt per mole of CuCN. The number of contact and separation steps may range from 1 to 5 but preferably in the range 2-4 steps. The total quantity of the bromide salt may be distributed equally or unequally among the aqueous solutions in the contact steps.

The salt concentration in the aqueous solutions may range from 30% to saturation but preferably in the range 40 to 50% w/w.

Alternatively, the contact and separation steps may be done continuously in a manner described below.

The quantity of the organic diluent may range from 0 to 300 ml per mole of p-halogenated phenol taken for reaction but preferably in the range 50-100 ml.

The temperature of the contact and separation stages may range from 70° to 100° C. but preferably from 80° to 95° C.

The temperature of the reaction between the alkali metal cyanide and the aqueous CuX solution may range from 20° to 95° C. but preferably between 40° and 70° C.

Preferred organic solvents for the reaction of p-halogenated phenol with cuprous cyanide comprise dimethylformamide, dimethylacetamide and N-methylpyrrolidone. Preferred organic diluents are the lower alkyl halides, such as chlorobromomethane, dibromomethane, ethylene dichloride, aromatic solvents such as benzene, toluene, xylene, chlorobenzene, and the like.

According to a preferred embodiment of the invention, the contact and separation steps of the process are effected continuously in a liquid-liquid extraction column, for example a column of the Karr type. Extraction in a Karr column is quicker and more energy efficient compared to conventional batch operations. Furthermore, extraction in a Karr column leads to an organic phase containing very low amounts of residual $Cu^+$, in the order of 200-2000 ppm. This, as will be apparent to the skilled chemist, is important in view of the purity requirements and maximum metal content levels acceptable for compounds of this kind. The preferred extraction solvent is toluene, although other aromatic solvents can also be employed. An advantage of toluene is that it is a good extraction solvent for dimethylacetamide, which renders it valuable in the process of the invention. As will be apparent to a person skilled in the art, the choice of the solvent will also influence the operating temperature of the extraction step, since this will be preferably effected at the temperature of reflux of the liquid mixture.

The above and other characteristics and advantages of the invention will be further illustrated by the following examples, which are not intended to constitute a limitation of the invention.

EXAMPLE 1

To a one liter three-necked flask equipped with a mechanical stirrer, a dropping funnel, a nitrogen inlet tube, a thermometer and a reflux condenser there were added 270 ml of DMA and 116.5 g of CuCN (1.3 mole). The contents of the flask were heated to reflux under a nitrogen atmosphere, and a solution of 173 g of p-bromophenol (1 mole) in 80 ml of DMA was added dropwise during 1.5 hours allowing the temperature to rise to 170° C. This temperature was maintained for an additional three hours, the flask was then equipped for vacuum distillation and 295 ml of DMA were distilled off.

After cooling the contents of the flask to 100° C., 500 ml of 48% aqueous sodium bromide and 100 ml of dibromomethane (DBM) were added. The mixture was stirred at 90° C. for 0.5 hour and the phases were separated. The organic phase was extracted with two additional 500 ml portions of 48% sodium bromide solution. This corresponds to a total of 8.3 moles of NaBr per mole of CuCN taken for the reaction. The residual Cu concentration was 580 ppm. The combined aqueous phases were washed with 100 ml of DBM and the DBM solution was added to the organic phase to give a solution containing 111.4 g of HBN (HPLC analysis), which corresponds to 93.6% of the theoretical yield. The product was isolated as a white crystalline solid, by vacuum distillation, in about 90% yield and 99% purity (HPLC).

A solution of 49 g of sodium cyanide (1 mole) in 112 ml of water was added during 0.5 hour to the combined aqueous phases at 50° C. The white suspension was stirred for an hour, cooled to 20° C. and filtered. The filter cake was washed with water and dried to give 105.0 g of CuCN containing 69.4% Cu corresponding to a recovery of 88.2% and a purity of 98.2%.

EXAMPLE 2

Example 1 was repeated, but using different diluents, salts and concentrations. The main conditions and results are set forth in Tables I through III below. Table II refers to the use of different salts with a given organic diluent, and Table III shows an example in which the concentration of the salt is decreased with any further extraction operation. This, as will be apparent to a skilled person, is possible since the copper concentration decreases after every extraction cycle. This experiment was also effected with no added organic diluent.

TABLE I

| | | | | | | | | | |
|---|---|---|---|---|---|---|---|---|---|
| | | Other Conditions and Results | | | | | | | |
| Org. diluent | | Aq. sol. of salt | | Aqueous solution (ml) for extraction | | HBN Yield | Recovered CuCN | | Residual copper in org. phase | moles salt mole CuCN |
| | ml | % in $H_2O$ | 1st | 2nd | 3rd | (%) | % Yield | Purity (%) | (ppm) | |
| DBM | 50 | 50% NaBr | 400 | 400 | 400 | 87.8 | 86.6 | 96.2 | 2700 | 7.0 |
| DBM | 50 | 48% NaBr | 500 | 330 | 170 | 85.7 | 98.9 | 95.1 | 1500 | 5.5 |
| toluene | 100 | 48% NaBr | 500 | 500 | 500 | 93.6 | 89.7 | 97.3 | 217 | 8.5 |

TABLE II

| | | | | | | | |
|---|---|---|---|---|---|---|---|
| | | Results With Different Salts | | | | | |
| Org. diluent | | Aq. sol. of salt % in $H_2O$ | Aqueous solution (ml) for extraction | | | Residual copper in org. phase | moles salt mole CuCN |
| | ml | | 1st | 2nd | 3rd | (ppm) | |
| toluene | 50 | 52% | 500 | 500 | 500 | 673 | 5.1 |

TABLE II-continued

Results With Different Salts

| Org. diluent | ml | Aq. sol. of salt % in H₂O | Aqueous solution (ml) for extraction | | | Residual copper in org. phase (ppm) | moles salt mole CuCN |
|---|---|---|---|---|---|---|---|
| | | | 1st | 2nd | 3rd | | |
| toluene | 50 | CaBr₂ 48% | 500 | 500 | 500 | 31 | 7.6 |
| toluene | 50 | NH₄Br 40% KBr | 500 | 500 | 500 | 605 | 5.3 |

TABLE III

Results With Decreasing Salt Concentration

| Aq. sol. of salt % in H₂O | Aqueous solution (ml) for extraction | | | Residual copper in org. phase (ppm) | moles salt mole CuCN |
|---|---|---|---|---|---|
| | 1st | 2nd | 3rd | | |
| 40% NaBr | 443 | — | — | | |
| 35% NaBr | — | 530 | — | | |
| 30% NaBr | — | — | 645 | 5000 | 5.6 |

EXAMPLE 3

Extraction in a Karr column

The Karr column consisted of a vertically mounted, glass tube 2 meters long, 50 mm in diameter and packed with a column of perforated (8 mm perforations) teflon discs. The discs were penetrated at the center by a teflon covered iron rod and were attached to the rod at 5 cm intervals, one from another, along the length of the rod. One end of the rod was linked to a motor in such a manner as to cause the rod and the attached discs to reciprocate along the axis of the tube. The frequency and amplitude of the movements of the rod and discs could be altered by adjusting the motor. Both ends of the Karr column were attached to glass tubes in which no disc were present. Theses tubes served as chambers in which the mixed phases could separate and could be removed continuously.

With the disc assembly of the Karr column moving with an amplitude of 3 mm and at 360 strokes per minute, organic phase from an HBN preparation containing 3.42% copper was introduced into the bottom portion of the column at a rate of 45 liters per hour while, simultaneously, an aqueous 48% sodium bromide solution was introduced into the upper portion of the column at 90 liters per hour. The operations were carried out at 90° C. The organic phase that separated and emerged from the column contained 0.18% copper.

Further examples using the Karr column are given in the following Table IV.

TABLE IV

| Ex. No. | Column Conditions | | | Flow Rate (l/h) | | Copper in Org. Phase (% w/w) | |
|---|---|---|---|---|---|---|---|
| | Amp. (mm) | Frequency strokes/min | Temp. °C. | Org. | Aq. | Before Extr. | After Extr. |
| 4 | 3 | 336 | 85 | 45 | 90 | 6.35 | 0.12 |
| 5 | 5 | 320 | 90 | 45 | 90 | 3.42 | 0.46 |
| 6 | 7 | 276 | 90 | 45 | 90 | 3.42 | 0.53 |
| 7 | 14 | 220 | 85 | 20 | 60 | 3.42 | 0.69 |

The above examples and descriptions have been given for the purpose of illustration, and are not intended to be limitative.

Many variations can be effected in the process described herein, without exceeding the scope of the invention.

We claim:

1. A method for recovering CuCN from a reaction mixture containing cuprous halide and p-hydroxybenzonitrile (HBN) in an organic solvent, comprising the steps of:
   (a) contacting said reaction mixture with an aqueous solution comprising about 30 percent by weight to saturation of a bromide salt, so that an organic phase comprising HBN and an aqueous phase comprising cuprous ions are formed;
   (b) separating said aqueous and organic phases;
   (c) adding an alkali metal cyanide to said aqueous phase, so that a precipitate of said CuCN is formed; and
   (d) separating said CuCN precipitate from said aqueous phase.

2. The method of claim 1, wherein said bromide salt is selected from the group consisting of sodium bromide, potassium bromide, calcium bromide and ammonium bromide.

3. The method of claim 2, wherein said bromide salt comprises sodium bromide or potassium bromide.

4. The method of claim 1, wherein said aqueous solution comprises from about 40% to about 50% by weight of said bromide salt.

5. The method of claim 1, wherein said aqueous solution further comprises an organic diluent.

6. The method of claim 5, wherein said organic diluent is selected from the group consisting of lower alkyl halides and aromatic solvents.

7. The method of claim 6, wherein said organic diluent is selected from the group consisting of chlorobromomethane, dibromomethane, ethylene dichloride, benzene, toluene, xylene and chlorobenzene.

8. The method of claim 1, wherein said alkali metal cyanide is added to said aqueous phase in an amount substantially stoichiometric with said cuprous halide.

9. The method of claim 1, wherein said alkali metal cyanide comprises sodium cyanide or potassium cyanide.

10. The method of claim 9, wherein said solvent comprises dimethylacetamide, said bromide salt comprises sodium bromide, and said alkali metal cyanide comprises sodium cyanide.

11. The method of claim 1, wherein said contacting and separating steps are carried out continuously.

12. The method of claim 11, wherein said contacting and separating steps are carried out in a column.

13. The method of claim 12, wherein said column is a Karr column.

14. The method of claim 1, wherein said reaction mixture is the product of a reaction employing CuCN recovered from a previous reaction cycle.

* * * * *

UNITED STATES PATENT AND TRADEMARK OFFICE
CERTIFICATE OF CORRECTION

PATENT NO.   :   5,294,416
DATED        :   March 15, 1994
INVENTOR(S)  :   Becker et al.

It is certified that error appears in the above-identified patent and that said Letters Patent is hereby corrected as shown below:

Column 1, line 23, "ArX + CuCn ⟶ ArCN + CuX" should read --ArX + CuCN ⟶ ArCN + CuX--.

Column 5, line 41, after "no disc were present.", "Theses tubes" should read --These tubes--.

Signed and Sealed this

Nineteenth Day of July, 1994

Attest:

BRUCE LEHMAN

Attesting Officer     Commissioner of Patents and Trademarks